United States Patent [19]

Dannehl

[11] 4,166,395
[45] Sep. 4, 1979

[54] TEST HEAD HOLDER IN A TEST SYSTEM CARRIER, PREFERABLY FOR ULTRASONIC TEST HEADS

[75] Inventor: Günther Dannehl, Dietzenbach, Fed. Rep. of Germany

[73] Assignee: Kraftwerk Union Aktiengesellschaft, Mülheim, Fed. Rep. of Germany

[21] Appl. No.: 857,701

[22] Filed: Dec. 5, 1977

[30] Foreign Application Priority Data

Dec. 6, 1976 [DE] Fed. Rep. of Germany ....... 2655179

[51] Int. Cl.² .............................................. G01N 29/04
[52] U.S. Cl. ..................................................... 73/634
[58] Field of Search ................. 73/620, 622, 623, 625, 73/629, 633, 634, 637, 638, 641, 644

[56] References Cited

U.S. PATENT DOCUMENTS

| | | | |
|---|---|---|---|
| 3,472,064 | 10/1969 | Kortenhoven | 73/634 |
| 3,534,591 | 10/1970 | Phelan | 73/644 X |
| 3,763,695 | 10/1973 | Zeiters | 73/638 |
| 3,863,496 | 2/1975 | Hiramatsu et al. | 73/634 |
| 3,952,582 | 4/1976 | Graham et al. | 73/637 |
| 4,033,178 | 7/1977 | Holt et al. | 73/644 |

FOREIGN PATENT DOCUMENTS

| | | | |
|---|---|---|---|
| 255105 | 2/1963 | Australia | 73/634 |
| 1795450 | 5/1959 | Fed. Rep. of Germany . | |

*Primary Examiner*—Anthony V. Ciarlante
*Attorney, Agent, or Firm*—Herbert L. Lerner

[57] ABSTRACT

In a test system carrier for non-destructive testing of a workpiece, a test head holder including means for moving a test head of the test system carrier and means for pressing the test head against a surface of the workpiece, the test head pressing means including a compressed air cylinder having a piston, a gimballed support body coupled to the piston for supporting the test head, the piston being actuatable to press the test head substantially perpendicularly against the surface of the workpiece.

5 Claims, 12 Drawing Figures

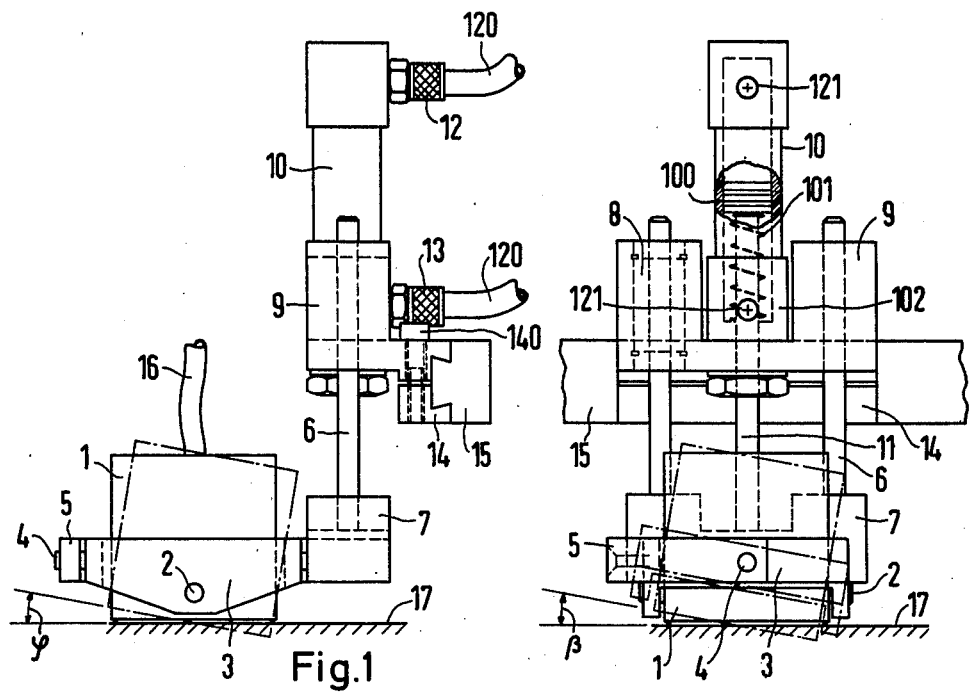
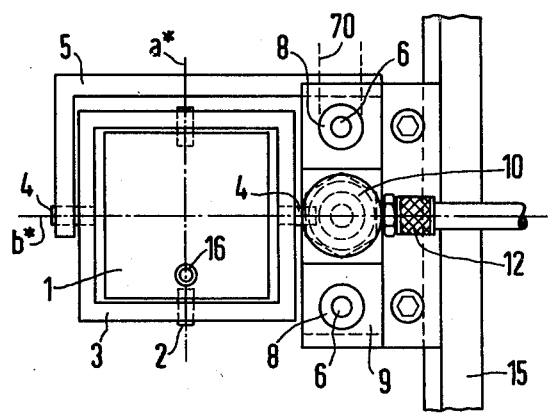
Fig.1
Fig.2
Fig.3

TEST HEAD HOLDER IN A TEST SYSTEM CARRIER, PREFERABLY FOR ULTRASONIC TEST HEADS

The invention relates to a test head holder in a test system carrier, preferably for ultrasonic test heads. For testing reactor pressure vessels in nuclear power plants, tests of the vessel material are required at periodic intervals; particularly the material of the welded seams and the thermally affected zones adjoining those seams must be checked. Remotely controllable testing instruments (manipulators) are preferably used for this purpose. Such testing instruments are predominantly equipped with ultrasonic test heads. Starting from one of the surfaces (inside or outside) of the vessel, the testing instruments test the volume of the material of the vessel wall as well as particularly highly stressed zones near the surface such as the inside edges of the coolant nozzle bores. These tests are performed primarily as comparative tests, it being therefore necessary that repeated tests be made with high reproducibility of the guidance and movement of the test heads. In special cases, such as curved test tracks in the vicinity of the nozzles, for example, it is necessary that the test heads perform rotary movements besides the movements in the longitudinal and transverse directions. These movements place stringent requirements on the test head holders. Unevenness of the test surface and changes of the spacing between the test head guidance plane and the test surfaces must not produce major deviations from the predetermined test head positions. In general, only a limited amount of space is available for the tests between the vessel and the shielding wall surrounding it. The determining part for the above-mentioned conditions is the holder which connects the test head per se to the testing device (manipulator).

All the heretofore known holders use springs as contact pressure means, with the typical distance-dependent force changes such as are known from spring diagrams, note, for example, the German Published Prosecuted Application DT-AS 2 153 397. In these conventional devices it is necessary to exchange the springs to vary the contact pressure.

In order to keep the force variations small, either the lever arms or the springs must be made longer, wherby considerable space is lost.

It is therefore an object of the invention of the instant application to overcome the aforedescribed shortcomings of the devices of this general type and to provide a device by which test heads, especially ultrasonic test heads, can be pressed against the surface to be tested with a constant force which is adapted to the structure of the surface, equalizing unevennesses without varying the contact pressure. Lateral displacement from the prescribed position when running over unevennesses is to be avoided. In addition, the holder should have an overall height as small as possible and occupy only a small area parallel to the test surface. The deviations from the prescribed positions due to the unavoidable bearing clearances should be kept as small as possible for the different movements, particularly for the rotary movement.

With the foregoing and other objects in view, there is provided, in accordance with the invention, in a test system carrier for non-destructive testing of a work piece, a test head holder comprising means for moving a test head of the test system carrier and means for pressing the test heads against a surface of the work piece, the test-head pressing means comprising a compressed-air cylinder having a piston, a gimballed support body coupled to the piston for supporting the test head the piston being actuatable to press the test head substantially perpendicularly against the surface of the work piece.

The advantages obtainable with the invention are seen primarily in the fact that the test head holder according to the invention can be used equally well for inside tests (immersion technology) as well as for outside tests (flow technology). The contact pressure of the test heads is produced for each test head by a separate compressed-air cylinder. The contact pressure can be varied by remote control by means of a reducing valve at the compressor or control unit. This is advantageous, for example, for testing surfaces with weld seams (inside overlay welding) only by the flow technology, i.e., with high flowing-water pressure and correspondingly high contact pressure.

In accordance with another feature of the invention, linear guide means are provided for guiding the gimballed support body in stroke direction of the piston, in a manner that the cylinder and piston are relieved of lateral forces exerted by the test head on the gimballed support body as the test head is slidingly moved over the surface of the work piece.

In accordance with an additional feature of the invention, the piston has a piston rod, and means are provided for fastening the support body to the piston rod.

In accordance with a further feature of the invention, the guiding means is in the form of two axially parallel linear guides having guide rods, each slidably secured to a guide body, the cylinder being rigid with the guide bodies and disposed axially parallel to the guide rods and intermediate the thereto.

In accordance with yet another feature of the invention, there is provided a compressed-air source, and supply lines connecting the compressed-air source to the cylinder, the volume of the cylinder being smaller than the volume of the supply lines and the volume of the compressed-air source. This is done so that the contact pressure is subjected only to minor, negligible changes when the stroke changes. This is particularly important when testing with the flow technology or technique and with high flowing-water pressure and correspondingly high contact pressure. Equally important in this regard is the precise lateral guidance.

In accordance with yet an additional feature of the invention, in order to prevent loss of coupling when moving over surfaces with a coarse structure, there is provided a test holder for ultrasonic test heads with flowing-water coupling of a test head to a workpiece having depressions, comprising means for increasing the contact pressure of the test head to the workpiece, means for increasing the flowing-water pressure and means for filling-in the depressions in the workpiece with water so as to maintain coupling between the test head and the workpiece.

In accordance with yet a further feature of the invention, there is provided separate means for supplying compressed-air to force the piston in opposite piston stroke directions.

In accordance with still another feature of the invention, there are provided means for spring-biasing the piston in one piston stroke direction, and means for supplying compressed air to force the piston against the biasing means in opposite piston stroke direction.

The compact construction of the test head holder according to the invention makes it possible to mutually align several test heads closely together in a row and even two or more rows closely together without limiting the mobility of the individual test heads. This is of particular importance for volume tests in thick vessel walls by means of tandem test head arrangements. If two or more parallel rows of test heads are used, the expensive and deadline-menacing test times are shortened and the required high testing standards are nevertheless maintained. For this purpose, there is provided, in accordance with still an additional feature of the invention, a multiplicity of test heads forming a test head row supported by a carrier arm in mutual alignment, each test head having a pneumatic drive unit and including means for equally pressing the multiplicity of test heads against the surface of the workpiece, the pressing means including a compressed air supply hose common to all of the test heads, and including linear guide means for guiding the gimballed support bodies in stroke direction of the respective piston in a manner that the respective cylinder and piston are relieved of lateral forces exerted by the test heads on the respective gimballed support body as the test heads are slidingly moved over the surface of the workpiece.

In accordance with still a further feature of the invention, a plurality of test head rows are structurally connected in parallel to each other to form a test head network.

The pneumatic system makes it possible, in addition, to lift the test heads of the test surface by remote control. Thereby, unnecessary wear of the runners or sliding surfaces of the test heads can be avoided when the test device executes large movements, without testing per se taking place. For this purpose, single-acting pneumatic cylinders with return springs suffice, for which reason the invention provides that the pistons can be acted upon unilaterally against the force of a return spring. If the test heads must overcome low obstacles (e.g. blisters, ledges etc.), then the test heads can be lifted quickly and in a programmed manner ahead of the obstacle through the use of double-acting pneumatic cylinders, which can be acted upon from either side.

In accordance with a concomitant feature of the invention, a multiplicity of test heads forming a test head row are supported by a carrier arm in mutual alignment, each test head having a pneumatic drive unit and including first means for equally pressing less than all of the multiplicity of test heads against the workpiece and second means for equally pressing at least one test head of the balance of the multiplicity of test heads against the workpiece, the first and second pressing means each including a separate common compressed air supply hose connected to a separate control valve, the separate control valve being connected to a compressed-air source.

Other features which are considered as characteristic for the invention are set forth in the appended claims.

Although the invention is illustrated and described herein as embodied in test head holder in a test system carrier, preferably for ultrasonic test heads, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawing, in which:

FIG. 1 is a diagrammatic side elevational view of the holder of a test head according to the invention, in fully extended condition with a representation of the swivel angle $\phi$, the position of the test head pivoted clockwise through the angle $\phi$ being shown in phantom, swivelling in counterclockwise or $-\phi$ direction being analogously also possible;

FIG. 2 is a front elevational view of the holder in fully extended condition with a representation of the tilt angle $\beta$, the tilt axis b* through the pivot pins 4 being rotated 90° with respect to the swivel axis a*, both these axes being shown in FIG. 3, and analogously tilting to both sides (clockwise and counterclockwise) being also possible, and the tilted position being likewise shown in phantom; also shown in FIG. 2 in phantom is an alternative embodiment of the invention having a return spring 101;

FIG. 3 is a top plan view of the holder;

FIGS. 6a and 6b are views similar to that of FIG. 2 of a chain of test heads, all of the test heads being in contact in FIG. 6a, whereas FIG. 6b shows an individual test head 10c of the chain in lifted position;

Figure 6A:
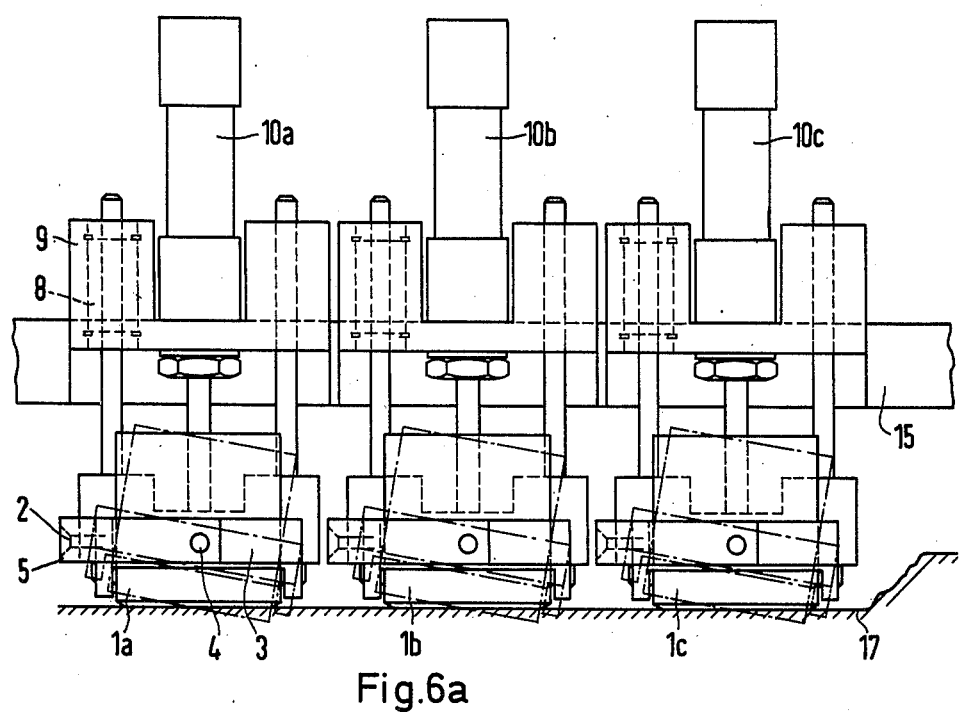
Figure 6B:
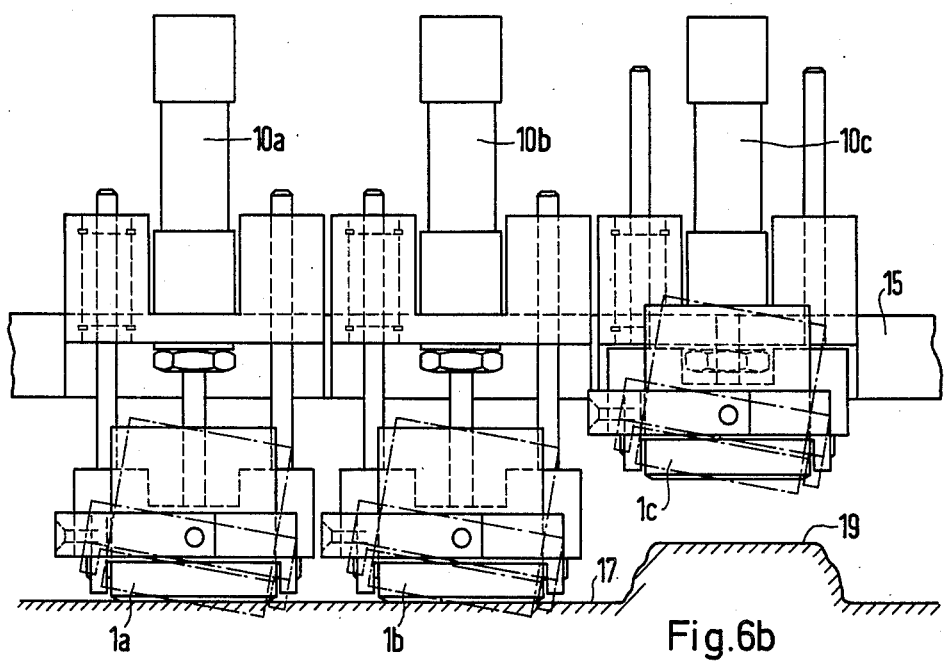
Figure 8A:
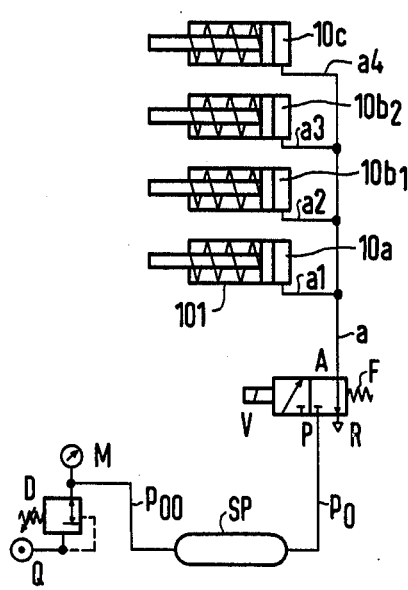
Figure 8B:
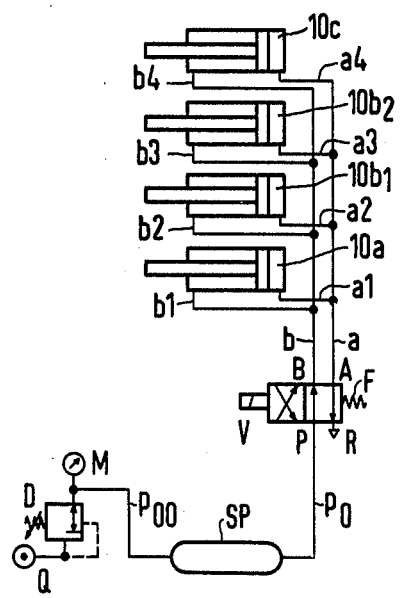
Figure 8C:
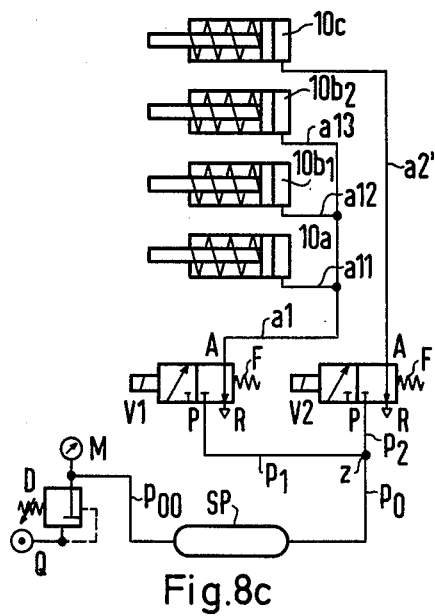
Figure 8D:
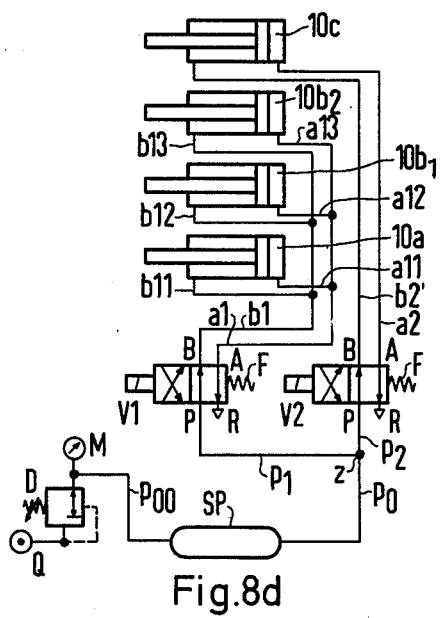

FIGS. 8a and 8d are different pneumatic circuit diagrams for the embodiment according to FIGS. 6a and 6b wherein, by dividing the pneumatic cylinder 10b of FIGS. 6a and 6b into two separate cylinders 10b1 and 10b2, there is meant that the number of pneumatic cylinders of a test head chain can be increased to more than 3 or can be decreased; more specifically, FIG. 8a is a circuit diagram of four single-acting pneumatic cylinders having return springs and common actuation;

FIG. 8b is a circuit diagram of four double-acting pneumatic cylinders with common actuation;

FIG. 8c is a circuit diagram of four single-acting pneumatic cylinders with return springs and separate actuation of the cylinder 10c; and FIG. 8d is a circuit diagram of four double-acting pneumatic cylinders with separate actuation of cylinder 10c.

Figure 4:
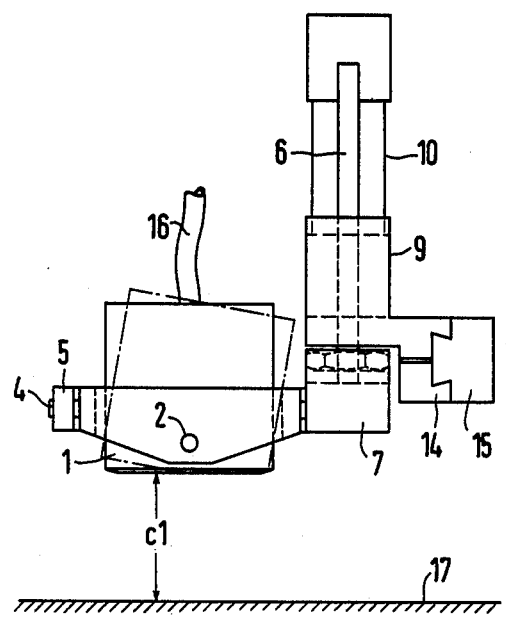
FIG. 4 is a side elevational view similar to that of FIG. 1 of the holder with the test head lifted, showing the amount of lift travel cl.
Figure 5:
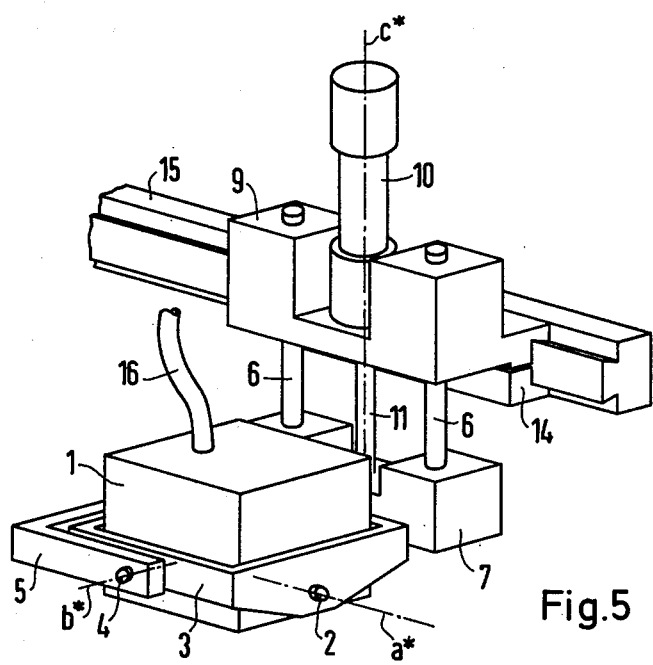
FIG. 5 is a perspective view of the holder showing the swivel, tilt and lift axes a*, b*, c*, respectively.

Referring now to the figures of the drawing and first, particularly to FIGS. 1 to 3 thereof, there is shown a test head 1 mounted by means of two mutually aligned pins 2 with a swivel axis a* in a rectangular gimbal frame 3, which is closed on itself. The gimbal frame 3, in turn, is mounted by means of two mutually aligned pins 4 with the tilting axis b* in a holding bracket 5 (see also FIG. 5). The holding bracket 5 is connected to the crosspiece 7 by two countersunk screws 70, shown in broken lines. Two guide rods 6 are firmly pinned in the crosspiece 7 and slide in the guide bushings 8 of a guide body 9. The guide bushings 8 must run freely and are therefore advantageously constructed as ball bushings. Between the guide bushings 8, which can generally also be called guide inserts, the guide body 9 carries a pneumatic cylinder 10 with a piston 100 (see FIG. 2), the piston rod 11 of which is bolted tightly to the crosspiece 7. Compressed air feed for pressing the test head 1 against a test surface 17 is affected through an upper hose connection 12; the test head 1 is lifted off the test surface 17, in a double-acting piston, by the application of pressure through the lower hose connection 13, which is omitted when a single-acting piston is employed. In a single-acting piston 100, on the other hand, the return spring 101, shown in broken lines (see FIG. 2) must be provided. The return spring 101 is braced with one end against the piston 100 and with the other end against a shoulder 102 of the cylinder 10. The cylinder 10 has compressed-air control openings 121.

The guide body 9 of the holder is adjustably fastened on the carrier arm 15 of the otherwise non-illustrated test system carrier (manipulator) with a clamping piece 14 by means of two screws 140. Flowing water from the water hose 16 is forced between the test head 1 and the test surface 17. The flowing water, together with the contact pressure from the pneumatic cylinder 10, effects a so-called "floating" and thereby permits easy sliding of the test head on rough and uneven surfaces, such as welded overlay seams and the like. During inside testing of a vessel filled with water (immersion technology), this flowing-water method is also required for very rough surfaces in order to obtain the "floating effect". In a test head chain (FIGS. 6a and 6b) and in a test head network arrangement (FIG. 7), the test heads 1a, 1b, 1c, etc. are supplied with compressed air through a common supply hose, all cylinders 10a, 10b, 10c, etc. exerting the same contact pressure on all the test heads 1a, 1b, 1c, etc. due to pressure equalization.

If individual cylinders of a test head chain are each supplied with compressed air through a separate supply hose, as will be explained hereinafter in further detail, it is possible to lift off and press down the test head 1c individually, for example, without affecting the other test heads 1a and 1b.

According to FIGS. 6a and 6b, several test heads (in the embodiment shown, the three test heads 1a, 1b and 1c) are each structurally combined with one support body formed of elements 2, 3, 4 and 5; one pneumatic drive unit 10a, 10b, 10c, respectively, as well as one rectilinear guide 8, 9, respectively, to form a test head row or test head chain. To this end, the just-mentioned members are fastened to the carrier arm 15 in alignment with one another. The separate pressing-down and lifting-off of the test head 1c is accomplished by means of separate compressed-air lines p2 and a2', as in FIG. 8c, for single-acting compressed-air cylinders, or p2, b2' and a2', as in FIG. 8d, for double-acting compressed-air cylinders. First, however, FIGS. 8a to 8d will be explained in principle, showing the required simple pneumatic circuits (with symbols in accordance with German Standards DIN 243000), where Q = source of compressed air (e.g. compressor)
D = adjustable regulating valve (pressure-reducing valve),
M = manometer (pressure indication)
SP = storage tank (employed here as an indication that between D and V the volume is substantially larger than that between cylinders 10a to c and V)
V, V1, V2 = control valves
A, B = consumer connections
P = pressure line generally
p1, p2, poo, po = specific pressure lines
R = venting line (relief opening)
F = return springs for valves V, V1, V2.

In FIGS. 8a and 8c, single-acting cylinders with return springs are shown. The valves V, V1 and V2 are electrically actuatable 3/2-way valves with return spring, 3/2 means a compressed-air valve with two switching positions represented by two square boxes within the rectangular valve and 2+1=3 inlets and outlets. These valves operate as follows: When the magnet is not energized (position shown), the pressure line P is shut off and the consumer connection A is vented through R. With the magnet energized (the box on the left-hand side containing the arrow is moved to the right-hand side), the pressure line P is connected to the consumer connection A, so that the pistons are driven out. This position is effective only as long as the magnet is energized. After the magnet voltage is removed, the valve V is automatically returned to the switching position shown.

In FIGS. 8b and 8d, double-acting cylinders are shown. The valves V, V1 and V2 are electrically operated 4/2-way valves with return springs. 4/2 means a compressed-air valve with two switching positions and 2+2=4 inlets and outlets. These valves operate as follows: With the magnet non-energized (position shown), the pressure line P is connected to the consumer connection B (return position of the pistons) and the consumer connection A is vented through R. With the magnet energized (left-hand box shifted to the right-hand side), the pressure line P is connected to the consumer connection A, so that the pistons are driven out, and the consumer connection B is now vented through R. This position is effective only as long as the magnet is energized. After the magnet voltage is removed, the valve V is automatically returned to the switching position shown.

In FIGS. 8a and 8b, all of the cylinders 10a and 10c are controlled by a common valve V. With the valve V switched on, pressure equalization between all cylinders up to the pressure regulating valve D is effected.

In FIGS. 8c and 8d, the cylinders 10c can be controlled, separately from the cylinders 10a and 10b2, by a valve V2 of their own. Control of the cylinders 10a to 10b2 is effected by the valve V1. Here, too, the pressure is equalized between all switched-on cylinders (either 10a to 10b2 or 10a to 10c) up to the pressure-regulating valve D.

The meaning of the other symbols is as follows:
poo = pressure line between D and SP
po = pressure line between SP and the branching point A
p1, p2 = pressure line between Z and, respectively, V1 and V2.

Furthermore, in FIGS. 8a and 8c:
a, a1 = main consumer lines
a1, a2, a3, a4 = consumer lines between a and 10a or 10b1 or 10b2 or 10c
a11, a12, a13 = consumer lines between a1 and 10a or 10b1 or 10b2, respectively,
a2' = separate consumer line between V2 and 10c In FIGS. 8b and 8dm there are in addition:
a, b, a1, b1 = main consumer lines,
b1, b2, b3, b4 = consumer lines to the one piston side of 10a or 10b1 or 10b2 or 10c, respectively,
a1, a2, a3, a4 = consumer lines to the other piston side of 10a or 10b1 or 10b2 or 10c, respectively,
b11, b12, b13 = consumer lines between b1 and the one piston side of 10a or 10b1 or 10b2, respectively; and a2′, b2′ = separate consumer lines between V2 and the one or the other piston side of the cylinder 10c.

The circuit diagram according to FIG. 8d shows a pneumatic circuit corresponding to FIGS. 6a and 6b, however, two cylinders 10b1 and 10b2 are shown, as aforementioned, instead of the one cylinder 10b according to FIGS. 6a and 6b. In both cases, the cylinder 10c is the separately acted-upon cylinder. In general, test head chains can be formed with n+1 cylinders (n=1, 2, 3 . . . ), where at least one thereof can always be separately controllable. Separate control can also be realized for single-acting pneumatic cylinders, as shown in FIG. 8c.

Figure 7:
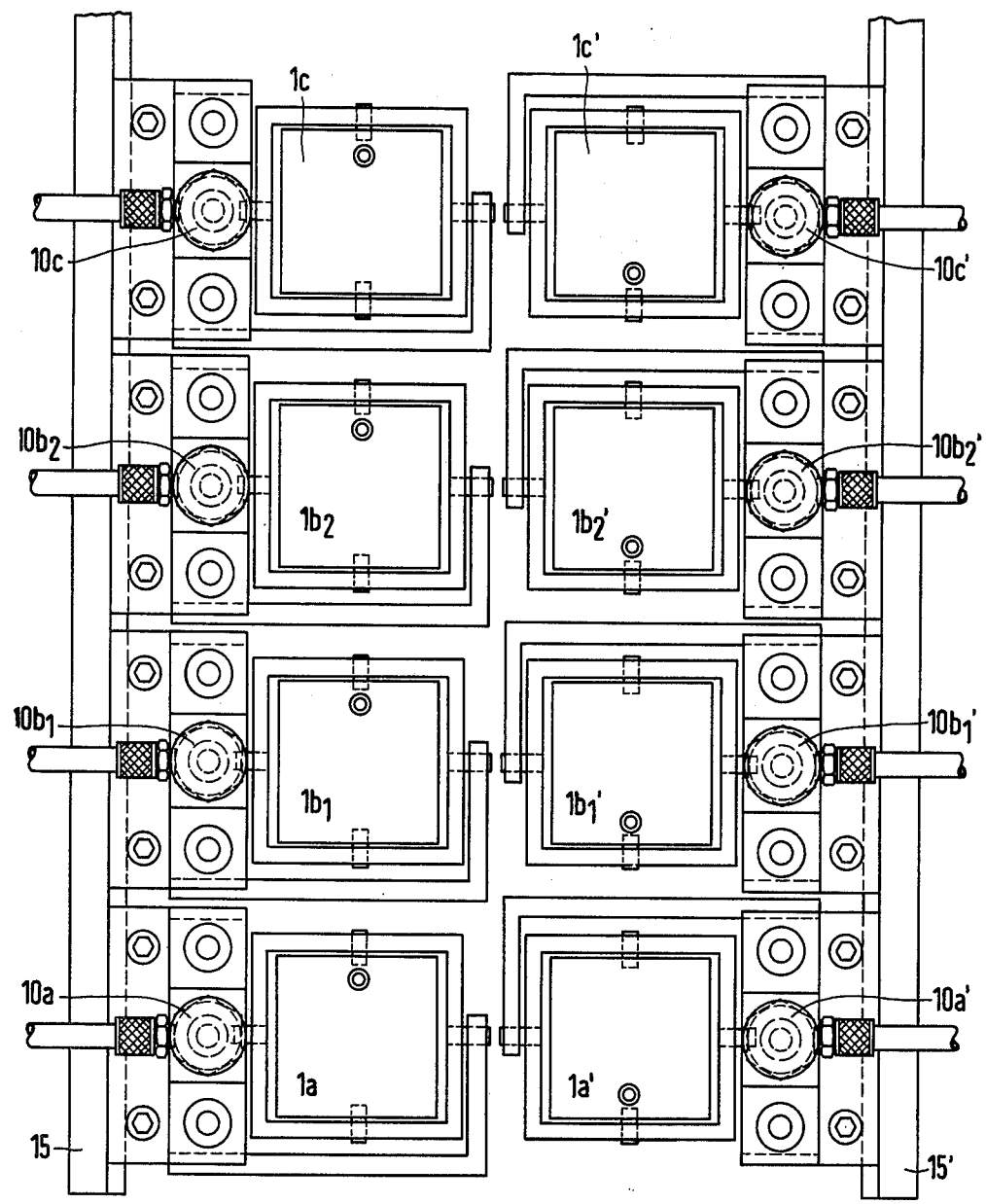
FIG. 7 is a top plan view of two test head rows disposed in parallel.

In the test head network according to FIG. 7, the corresponding compressed-air control circuit is not shown. However, it should be understood that one of the circuits according to FIGS. 8a to 8d can be used analogously and that, if the circuits according to FIGS. 8c and 8d are used properly, individual compressed-air cylinders 10a to 10c or 10a′ to 10c′ can be actuatable separately. In this way, individual test heads 1a to 1c or 1a′ to 1c′ can be seatable or liftable off, separated from the other test heads. The test head network can be thought of here as produced by two test head chains, as shown in FIGS. 6a and 6b by increasing the number of test heads per chain from three to four, the carrier arms 15 and 15′ being mounted on a common non-illustrated holder.

There is claimed:

1. In a test system carrier having a test head for non-destructive testing of a workpiece, a test head holder comprising means for moving the test head over and means for pressing the test head against a surface of the workpiece, said test-head pressing means comprising a compressed-air cylinder having a piston, a support body for supporting the test head, gimbal means coupling said support body to said piston, said piston being actuatable to press the test head substantially perpendicularly against the surface of the workpiece and linear guide means for guiding said support body in stroke direction of the piston, in a manner that said cylinder and piston are relieved of lateral forces exerted by the test head on said support body as the test head is slidingly moved over the surface of the workpiece, said linear guide means being in the form of two axially parallel linear guides having guide rods, each slidably secured to a guide body, said cylinder being rigid with said guide bodies and disposed axially parallel to said guide rods and intermediate thereto.

2. Test head holder according to claim 1, wherein a multiplicity of test heads forming a test head row are supported by a carrier arm in mutual alignment, each test head having a pneumatic drive unit and including means for equally pressing said multiplicity of test heads against the surface of the workpiece, said pressing means including a compressed-air supply hose common to all of the test heads, and including linear guide means for guiding the gimballed support bodies in stroke direction of the respective piston in a manner that the respecitve cylinder and piston are relieved of lateral forces exerted by the test heads on the respective gimballed support body as the test heads are slidingly moved over the surface of the workpiece.

3. Test head holder according to claim 2, wherein a plurality of test head rows are structurally connected in parallel to each other to form a test head network.

4. In a test system carrier having a test head for nondestructive testing of a workpiece, a test head holder comprising means for moving the test head over and means for pressing the test head against a surface of the workpiece, said test-head pressing means comprising a compressed-air cylinder having a piston, a support body for supporting the test head, gimbal means coupling said support body to said piston, said piston being actuatable to press the test head substantially perpendicularly against the surface of the workpiece, including a compressed-air source, and supply lines connecting said compressed-air source to said cylinder, the volume of said cylinder being smaller than the volume of said supply lines and the volume of said compressed-air source.

5. In a test system carrier having a test head for nondestructive testing of a workpiece, a test head holder comprising means for moving the test head over and means for pressing the test head against a surface of the workpiece, said test-head pressing means comprising a compressed-air cylinder having a piston, a support body for supporting the test head, gimbal means coupling said support body to said piston, said piston being actuatable to press the test head substantially perpendicularly against the surface of the workpiece and linear guide means for guiding said support body in stroke direction of the piston, in a manner that said cylinder and piston are relieved of lateral forces exerted by the test head on said support body as the test head is slidingly moved over the surface of the workpiece, wherein a multiplicity of test heads forming a test head row are supported by a carrier arm in mutual alignment, each test head having a pneumatic drive unit and including first means for equally pressing less than all of the multiplicity of test heads against the workpiece and second means for equally pressing at least one test head of the balance of the multiplicity of test heads against the workpiece, said first and second pressing means each including a separate common compressed-air supply hose connected to a separate control valve, said separate control valves being connected to a compressed-air source.

* * * * *